United States Patent [19]

Huang

[11] 4,441,990

[45] Apr. 10, 1984

[54] HOLLOW SHAPED CATALYTIC EXTRUDATES

[75] Inventor: Yun-Yang Huang, Voorhees, N.J.

[73] Assignee: Mobil Oil Corporation, New York, N.Y.

[21] Appl. No.: 383,070

[22] Filed: May 28, 1982

[51] Int. Cl.³ .................. C10G 47/02; B01J 35/00; C07C 2/68; C07C 2/02
[52] U.S. Cl. ........................... 208/111; 208/120; 502/527; 585/467; 585/475; 585/481; 585/533; 585/640
[58] Field of Search ............... 252/477 R; 585/467, 585/475, 481, 533, 640; 208/111, 120

[56] References Cited

U.S. PATENT DOCUMENTS

| | | | |
|---|---|---|---|
| 3,674,680 | 7/1972 | Hoekstra et al. | 252/477 R |
| 3,966,644 | 6/1976 | Gustafson | 252/477 R |
| 4,076,888 | 2/1978 | Perugini et al. | 252/477 R |
| 4,083,888 | 4/1978 | Caesar et al. | 585/640 |
| 4,097,543 | 6/1978 | Haag et al. | 585/475 |
| 4,324,940 | 4/1982 | Dessau | 585/467 |
| 4,328,130 | 5/1982 | Kyan | 252/477 R |

*Primary Examiner*—Curtis R. Davis
*Attorney, Agent, or Firm*—Alexander J. McKillop; Michael G. Gilman; Charles J. Speciale

[57] ABSTRACT

The present invention relates to novel cross-section shapes which are employed to form catalytic extrudates which may be employed in catalytically promoted processes including hydrocarbon processing operations. Such shapes include essentially rectangular shaped tubes, and triangular shaped tubes in cross section.

39 Claims, 7 Drawing Figures

HOLLOW SHAPED CATALYTIC EXTRUDATES

FIELD OF THE INVENTION

The present invention relates to novel shaped formed particles which may be employed in a wide variety of catalytically activated and/or enhanced processes including, for example, alkylation or dealkylation of aryl compounds including benzene; the isomerization of various materials including, for example, xylene; and in the conversion of substances such as coal derived compounds or methanol or other hydrocarbons into materials, such as olefins, or fuels or lubricants and the like. The particular configuration of the formed particle is selected to optimize the catalytic activity and physical properties such as pressure drop, crushing strength and abrasion resistance of the particle as well as the selectivity of the catalyst for the particularly desired product. The novel shaped formed particles of the present invention may also be employed for end use applications including guard bed service and/or as catalyst supports.

BACKGROUND OF THE INVENTION

It has been known in the past that by selection of varied geometrical cross sectional configurations, formed catalytic particles may be designed to offer shorter diffusion paths for reactants and/or products which may be desirable in, for example, a diffusion controlled reaction. Additionally, catalytic particle configuration has been employed in the past to reduce the pressure drop encountered across a packed catalyst bed, and/or to reduce catalyst loss due to breakage, abrasion or crushing during handling, sizing or when severe process conditions are encountered. As a specific example, tubular extrudates have been employed in the past to improve the surface area-diffusion path presented by such catalytic particles, as well as to reduce the pressure drop encountered when reactants are passed through a catalytic bed. However, such tubular, cylindrical extrudates have the disadvantage of low crushing strength whereby during handling or use fracturing of the delicate tubular cylindrical structures results in fragmentation of the catalyst particle which will result in pressure drop increases in certain instances. The novel shapes of the present invention exhibit greater fracture resistance and, additionally, have a reduced tendency toward end blockage by an adjacent particle in a randomly packed catalyst bed when compared to prior art tubular cylinder structures.

In accordance with one aspect of the present invention, novel tubular extrudate cross sectional configurations are provided which are specifically designed to reduce catalyst loss due to breakage, abrasion, or crushing forces which may be encountered in handling, sizing or under severe process conditions. It has been shown in the past that by intentionally altering the shapes of formed particles from that most often utilized in fixed bed applications i.e. a solid cylinder, the pressure drop or resistance to flow encountered across said bed can be reduced. In the case of formed catalytic particles, configurational changes so alter the surface to volume ratio that the resultant design offers shorter diffusion paths for reactants and/or products which may be desirable in, for example, a diffusion controlled catalytic reaction. Alternatively, changes in particle forms have been employed in the past to reduce loss due to breakage, abrasion or crushing during handling, sizing or when severe process conditions are encountered.

As a specific example, the prior art discloses that tubular extrudates, i.e. formed particles possessing both cylindrical external perimeters and cylindrical internal cores or holes reduce the pressure drop across a packed bed of the same height relative to solid cylinders by virtue of the increase in bed void volume. Additionally in catalytic applications these tubular shaped entities have been employed to improve heat and mass trasfer rates by virtue of their surface to volume enhancement, where such factors are controlling. However, such tubular, cylindrical extrudates have the disadvantage of low crushing strength relative to their solid counterparts. Consequentially, during handling or use fracturing of the delicate tubular cylindrical structures results in fragmentation of the particles which, in commercial applications, ultimately results in increased pressure drop as a result of an increase in resultant fines or dust. Conversely, the neoteric shapes of the present invention offer improvements in the resistance to fluid flow or pressure drop across a packed bed, and also improvements in heat and mass trasfer properties as a consequence of their favorable surface to volume ratios, which improvements are of special significance in catalytic applications. In addition, and entirely unexpected, the unique shapes herein below described, simultaneously exhibit a resistance to loss due to breakage, abrasion or crushing forces which may be encountered in handling, sizing or under severe process conditions. Consequently, the extrudate shapes in accordance with the present invention offer, by design, improvement over solid, i.e. non-tubular, cross sections with respect to reduced pressure drop across a fixed bed, and at least one or more of these shapes also evidences a reduced tendency toward end blockage by an adjacent particle in a ramdonly packed bed.

For purposes of the present invention "tubular" is intended to include configurations which in addition to hollow cylinders include hollow or apertured structures having non-circular external perimeters, e.g. rectangular, triangular or other geometrical configurations such as multiple bulbous protrusions connected by concave surfaces or the like, specific examples of which are shown in the accompanying Figures and Drawings.

SUMMARY OF THE INVENTION

In accordance with the present invention catalyst particles are provided having a centrally located aperture surrounded by a solid wall portion, a volume to surface ratio of less than 0.02 inch, and an external periphery characterized by having at least 3 and no more than 10, preferably no more than 4 points of contact when circumscribed by a cylindrical shape.

DESCRIPTION OF SPECIFIC EMBODIMENTS

The novel tubular catalyst extrudates in accordance with the present invention exhibit the following advantages:

(1) Greater particle surface area per unit volume and shorter diffusion path for reactants and/or products.

(2) Reduced pressure drop across a packed catalyst bed; and (3) Reduced catalyst loss due to breakage, abrasion, or crushing in handling, sizing, or under severe process conditions.

As hereinabove discussed, although the prior art cylindrical tube extrudates in some cases may exhibit advantages (1) and (2) noted hereinabove, they lack high crushing strength. The novel catalyst particle shapes in accordance with the present invention, by virtue of the increased number of points of contact with one another, when a load is applied, these catalyst particles radically alter the load distribution of the particle. Consequently, the novel shaped tubular catalytic extrudates in accordance with the present invention have been found to sustain crush or load per unit volume far greater than the prior art cylindrical tubular particle configurations.

It is known that certain reactions which require solid catalysts in the form of particles are limited by the rate of diffusion of the reactants into the particle and by the rate of the diffusion of the products formed by the reactants out of the particle. Accordingly, there is an advantage in making the particles so that they exhibit a high surface area to volume ratio. This may be achieved by reducing the particle size; however, there is a practical lower limit to the size of the particle since as the particle size decreases the pressure drop required to pump the reactants through the catalyst bed increases. Also, prior art shapes are difficult to manufacture in diameters less than 1/32 inch as well as their physical strength characteristics being so poor as to be commercially unacceptable.

According to the present invention, there is provided a shaped catalyst particle having an aperture formed through the central portion thereof.

According to another preferred embodiment of the present invention, there is provided a catalyst particle in a novel form which has protrusions at the areas where its sides are joined together. Further, the protrusions may be bulbous as in the case of the configuration shown in FIG. 1; or rounded as in the case of the corners of the configurations shown in FIGS. 2 and 3. Although for purposes of illustration these corners have been shown as being rounded rather than pointed or sharp, it will be understood that such sharp edges or corners have been rounded off, for example, to facilitate manufacture and increase wear-resistance, but there may be instances where sharp edges or corners are more desirable and accordingly are included within the scope of the present invention.

Figure 1:
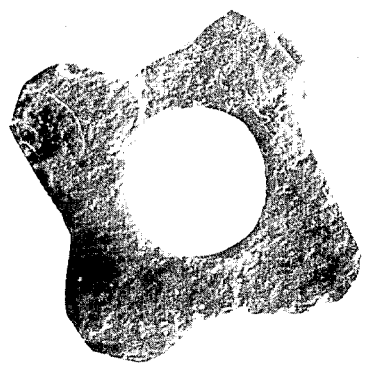
FIG. 1 is a photolithographic reproduction of a cross section of a preferred form of catalyst particle in accordance with the present invention.
Figure 4:
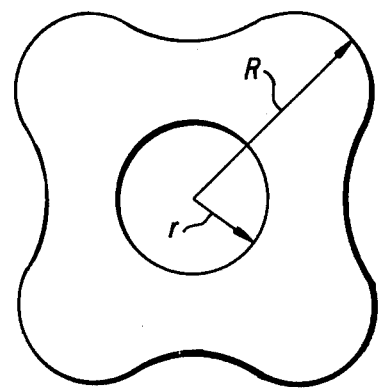
FIG. 4 is a graphic representation of the specific embodiment of catalyst particle form as illustrated in FIG. 1.
Figure 5:
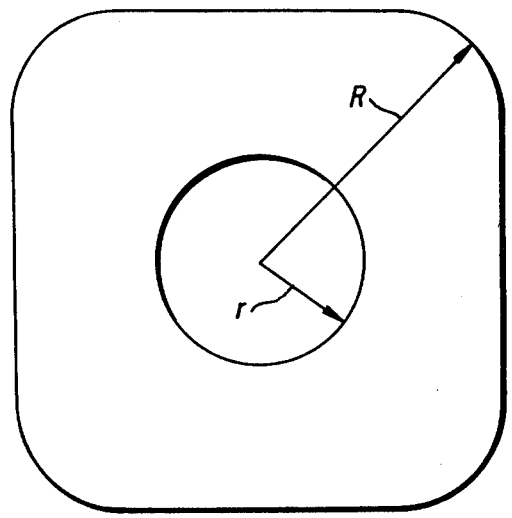
FIG. 5 is a graphic representation of the catalyst particle form as illustrated in FIG. 2.
Figure 6:
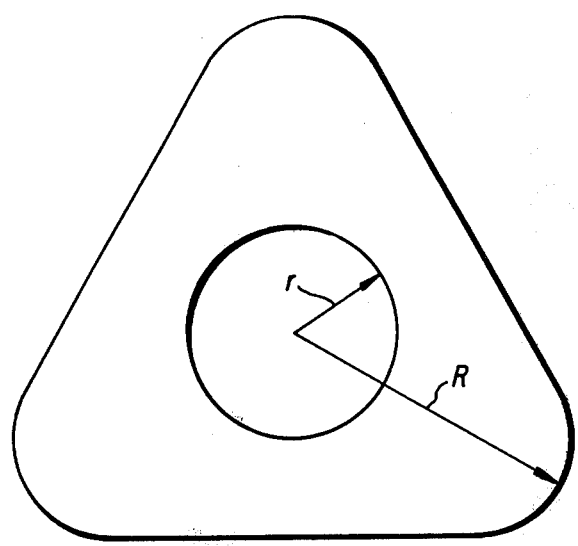
FIG. 6 is a graphic representation of the catalyst particle form as illustrated in FIG. 3.

It will be noted that particle configuration as shown in FIGS. 1 and 4 is characterized by having bulbous protrusions around the external periphery. It will be further noted that these protursions are continuous in that the areas between the individual bulbs are continuously concave whereby each protrusion contiuously flows into an adjacent one in a smooth manner without any abrupt discontinuity or pronounced angular-like interruptions.

As shown in the accompanying Figures and drawings, R is the radius of a hypothetical cylinder which circumscribes the particle. The maximum thickness of the wall may vary in a ratio of $R/r$ from about 1.1 up to about 10 and preferably from about 1.5 to 5 and even more preferably from about 2 to about 3.

It will also be noted that there may be certain optimum wall thicknesses dependent upon the individual process applications. For example, in processes, which are significantly effected by heat and mass transfer, wall thickness on the order from about $\frac{1}{8}$ inch or less and preferably 1/10 inch or less and even more preferably about 1/25 inch or less are preferable in such diffusion controlled reactions.

The cross-sectional configuration of the catalyst particles according to the present invention may be defined by means of a number of various parameters. For example, r may be defined as the particle aperture radius and R may be defined as the maximum distance from the center of the aperture to the wall outer periphery. The wall thickness will vary depending upon the particular tubular cross-section configuration of the particle. In the case of the prior art cylindrical tube configuration shown in FIG. 7, assuming a uniformly dimensioned hollow cylinder, the wall thickness remains constant.

The novel catalyst particle configurations of the present invention are usefully employed in catalyst structures for heterogeneous reactions, for examples, support materials such as the difficultly reducible oxides of Groups II to IV of the Periodic Table including hydraulic cements, catalytically active oxides such as silica, alumina and oxides from Group V–VIII of the Periodic Table, and metals from Group IB and VIII of the Periodic Table. Catalysts are contemplated in the scope of the present invention which contain no added metal as well as catalysts which contain added metal. Metals such as, for example, nickel, platinum, silver, and the like. The catalyst particles of the present invention may comprise alumina or alumina as a support in admixture with a zeolite. Useful catalyst also include those containing cobalt and molybdenum oxides and copper and zinc oxides. The constituents may be all present at the time of shaping or may be practically added afterwards, for example, by impregnation.

As hereinbefore indicated, a wide variety of catalytic compositions may be employed utilizing the novel particle structures in accordance with the present invention including catalysts which comprise a crystalline aluminosilicate zeolites. Such zeolites may have contained within their internal crystalline structure other materials such as, for example, amorphous silica, $Fe_2O_3$, $B_2O_3$, $P_2O_5$, and the like.

The crystalline zeolites which may be employed in accordance with the present invention are members of a class of zeolitic materials which exhibit unusual properties. Although these zeolites have unusually low alumina contents, i.e. high silica to alumina mole ratios, they are very active even when the silica to alumina mole ratio exceeds 30. The activity is surprising since catalytic activity is generally attributed to framework aluminum atoms and/or cations associated with these aluminum atoms. These zeolites retain their crystallinity for long periods in spite of the presence of steam at high temperature which induces irreversible collapse of the framework of other zeolites, e.g. of the X and A type. Furthermore, carbonaceous deposits, when formed, may be removed by burning at higher than usual temperatures to restore activity. These zeolites, used as catalysts, generally have low coke-forming activity and therefore are conducive to long times on stream between regenerations by burning carbonaceous deposits with oxygen-containing gas such as air.

An important characteristic of the crystal structure of this class of zeolites is that it provides a selective constrained access to and egress from the intracrystalline free space by virtue of having an effective pore size intermediate between the small pore Linde A and the large pore Linde X, i.e. the pore windows of the structure are of about a size such as would be provided by 10-membered rings of silicon atoms interconnected by oxygen atoms. It is to be understood, of course, that these rings are those formed by the regular disposition of the tetrahedra making up the anionic framework for the crystalline zeolite, the oxygen atoms themselves being bonded to the silicon (or aluminum, etc.) atoms at the centers of the tetrahedra.

The silica to alumina mole ratio referred to may be determined by conventional analysis. This ratio is meant to represent, as closely as possible, the ratio in the rigid anionic framework of the zeolite crystal and to exclude aluminum in the binder or in cationic or other form within the channels. Although zeolites with silica to alumina mole ratios of at least 12 are useful, it is preferred in some instances to use zeolites having substantially higher silica/alumina ratios, e.g. 1600 and above. In addition, zeolites as otherwise characterized herein but which are substantially free of aluminum, that is zeolites having silica to alumina mole ratios of up to infinity, are found to be useful and even preferable in some instances. Such "high silica" or "highly siliceous" zeolites are intended to be included within this description. Also included within this definition are substantially pure silica analogs of the useful zeolites described herein, that is to say those zeolites having no measurable amount of aluminum (silica to alumina mole ratio of infinity) but which otherwise embody the characteristics disclosed.

The novel class of zeolites, after activation, acquire an intracrystalline sorption capacity for normal hexane which is greater than that for water, i.e. they exhibit "hydrophobic" properties. This hydrophobic character can be used to advantage in some applications.

The novel class of zeolites useful herein have an effective pore size such as to freely sorb normal hexane. In addition, the structure must provide constrained access to larger molecules. It is sometimes possible to judge from a known crystal structure whether such constrained access exists. For example, if the only pore windows in a crystal are formed by 8-membered rings of silicon and aluminum atoms, then access by molecules of larger cross-section than normal hexane is excluded and the zeolite is not of the desired type. Windows of 10-membered rings are preferred, although in some instances excessive puckering of the rings or pore blockage may render these zeolites ineffective.

Although 12-membered rings in theory would not offer sufficient constraint to produce advantageous conversions, it is noted that the puckered 12-ring structure of TMA offretite does show some constrained access. Other 12-ring structures may exist which may be operative for other reasons and, therefore, it is not the present intention to entirely judge the usefulness of a particular zeolite solely from theoretical structural considerations.

Rather than attempt to judge from crystal structure whether or not a zeolite possesses the necessary constrained access to molecules of larger cross-section than normal paraffins, a simple determination of the "Constraint Index" as herein defined may be made by passing continuously a mixture of an equal weight of normal hexane and 3-methylpentane over a sample of zeolite at atmospheric pressure according to the following procedure. A sample of the zeolite, in the form of pellets or extrudate, is crushed to a particle size about that of coarse sand and mounted in a glass tube. Prior to testing, the zeolite is treated with a stream of air at 540° C. for at least 15 minutes. The zeolite is then flushed with helium and the temperature is adjusted between 290° C. and 510° C. to give an overall conversion of between 10% and 60%. The mixture of hydrocarbons is passed at 1 liquid hourly space velocity (i.e., 1 volume of liquid hydrocarbon per volume of zeolite per hour) over the zeolite with a helium dilution to give a helium to (total) hydrocarbon mole ratio of 4:1. After 20 minutes on stream, a sample of the effluent is taken and analyzed, most conveniently by gas chromatography, to determine the fraction remaining unchanged for each of the two hydrocarbons.

While the above experimental procedure will enable one to achieve the desired overall conversion of 10 to 60% for most zeolite samples and represents preferred conditions, it may occasionally be necessary to use somewhat more severe conditions for samples of very low activity, such as those having an exceptionally high silica to alumina mole ratio. In those instances, a temperature of up to about 540° C. and a liquid hourly space velocity of less than one, such as 0.1 or less, can be employed in order to achieve a minimum total conversion of about 10%.

Also intended to be within the scope of the present invention are zeolites such as zeolite X and Y; ZSM-Beta, mordenite and erionite.

The "Constraint Index" is calculated as follows:

Constraint Index =

$$\frac{\log_{10} \text{(fraction of hexane remaining)}}{\log_{10} \text{(fraction of 3-methylpentane remaining)}}$$

The Constraint Index approximates the ratio of the cracking rate constants for the two hydrocarbons. Zeolites suitable for the present invention are those having a Constraint Index of 1 to 12. Constraint Index (CI) values for some typical materials are:

|  | C.I. |
|---|---|
| ZSM-4 | 0.5 |
| ZSM-5 | 8.3 |
| ZSM-11 | 8.7 |
| ZSM-12 | 2 |
| ZSM-23 | 9.1 |
| ZSM-35 | 4.5 |
| ZSM-38 | 2 |
| ZSM-48 | 3.4 |
| TMA Offretite | 3.7 |
| Clinoptilolite | 3.4 |
| Beta | 0.6 |
| H—Zeolon (mordenite) | 0.4 |
| REY | 0.4 |

| | C.I. |
|---|---|
| Amorphous Silica-Alumina | 0.6 |
| Erionite | 38 |

The above-described Constraint Index is an important and even critical definition of those zeolites which are useful in the instant invention. The very nature of this parameter and the recited technique by which it is determined, however, admit of the possibility that a given zeolite can be tested under somewhat different conditions and thereby exhibit different Constraint Indices. Constraint Index seems to vary somewhat with severity of operation (conversion) and the presence or absence of binders. Likewise, other variables such as crystal size of the zeolite, the presence of occluded contaminants, etc., may affect the constraint index. Therefore, it will be appreciated that it may be possible to so select test conditions as to establish more than one value in the range of 1 to 12 for the Constraint Index of a particular zeolite. Such a zeolite exhibits the constrained access as herein defined and is to be regarded as having a Constraint Index in the range of 1 to 12. Also contemplated herein as having a Constraint Index in the range of 1 to 12 and therefore within the scope of the defined novel class of highly siliceous zeolites are those zeolites which, when tested under two or more sets of conditions within the above-specified ranges of temperature and conversion, produce a value of the Constraint Index slightly less than 1, e.g. 0.9, or somewhat greater than 12, e.g. 14 or 15, with at least one other value within the range of 1 to 12. Thus, it should be understood that the Constraint Index value as used herein is an inclusive rather than an exclusive value. That is, a crystalline zeolite when identified by any combination of conditions within the testing definition set forth herein as having a Constraint Index in the range of 1 to 12 is intended to be included in the instant novel zeolite definition whether or not the same identical zeolite, when tested under other of the defined conditions, may give a Constraint Index value outside of the range of 1 to 12.

The novel class of zeolites defined herein is exemplified by ZSM-5, ZSM-11, ZSM-12, ZSM-23, ZSM-35, ZSM-38, ZSM-48, and other similar materials.

ZSM-5 is described in greater detail in U.S. Pat. Nos. 3,702,886 and Re 29,948. The entire descriptions contained within those patents, particularly the X-ray diffraction pattern of therein disclosed ZSM-5, are incorporated herein by reference.

ZSM-11 is described in U.S. Pat. No. 3,709,979. That description, and in particular the X-ray diffraction pattern of said ZSM-11, is incorporated herein by reference.

ZSM-12 is described in U.S. Pat. No. 3,832,449. That description, and in particular the X-ray diffraction pattern disclosed therein, is incorporated herein by reference.

ZSM-23 is described in U.S. Pat. No. 4,076,842. The entire content thereof, particularly the specification the X-ray diffraction pattern of the disclosed zeolite, is incorporated herein by reference.

ZSM-35 is described in U.S. Pat. No. 4,016,245. The description of that zeolite, and particularly the X-ray diffraction pattern thereof, is incorporated herein by reference.

ZSM-38 is more particularly described in U.S. Pat. No. 4,046,859. The description of that zeolite, and particularly the specified X-ray diffraction pattern thereof, is incorporated herein by reference.

ZSM-48 can be identified, in terms of moles of anhydrous oxides per 100 moles of silica, as follows:

(0-15)RN: (0-1.5)$M_{2/n}$O: (0.2)$Al_2O_3$: (100)$SiO_2$ wherein:
M is at least one cation having a valence n; and
RN is a $C_1$-$C_{20}$ organic compound having at least one amine functional group of $pK_a < 7$.

It is recognized that, particularly when the composition contains tetrahedral framework aluminum, a fraction of the amine functional groups may be protonated. The doubly protonated form, in conventional notation, would be $(RNH)_2O$ and is equivalent in stoichiemetry to $2RN + H_2O$.

The characteristic X-ray diffraction pattern of the synthetic zeolite ZSM-48 has the following significant lines:

| Characteristic Lines of ZSM-48 | |
|---|---|
| d (Angstroms) | Relative Intensity |
| 11.9 | W-S |
| 10.2 | W |
| 7.2 | W |
| 5.9 | W |
| 4.2 | VS |
| 3.9 | VS |
| 3.6 | W |
| 2.85 | W |

These values were determined by standard techniques. The radiation was the K-alpha doublet of copper, and a scintillation counter spectrometer with a strip chart pen recorder was used. The peak heights, I, and the positions as a function of 2 times theta, where theta is the Bragg angle, were read from the spectrometer chart. From these, the relative intensities, 100 $I/I_o$, where $I_o$ is the intensity of the strongest line or peak, and d (obs.), the interplanar spacing in angstroms, corresponding to the recorded lines, were calculated. In the foregoing table the relative intensities are given in terms of the symbols W=weak, VS=very strong and W-S=weak-to-strong. Ion exchange of the sodium ion with cations reveals substantially the same pattern with some minor shifts in interplanar spacing and variation in relative intensity. Other minor variations can occur depending on the silicon to aluminum ratio of the particular sample, as well as if it has been subjected to thermal treatment.

The ZSM-48 can be prepared from a reaction mixture containing a source of silica, water, RN, an alkali metal oxide (e.g. sodium) and optionally alumina. The reaction mixture should have a composition, in terms of mole ratios of oxides, falling within the following ranges:

| REACTANTS | BROAD | PREFERRED |
|---|---|---|
| $Al_2O_3/SiO_2$ | 0 to 0.02 | 0 to 0.01 |
| $Na/SiO_2$ | 0 to 2 | 0.1 to 1.0 |
| $RN/SiO_2$ | 0.01 to 2.0 | 0.05 to 1.0 |
| $OH^-/SiO_2$ | 0 to 0.25 | 0 to 0.1 |
| $H_2O/SiO_2$ | 10 to 100 | 20 to 70 |
| $H^+$(added)$/SiO_2$ | 0 to 0.2 | 0 to 0.05 | wherein RN is a $C_1$–$C_{20}$ organic compound having amine functional group of $pK_a \leq 7$. The mixture is maintained at 80°–250° C. until crystals of the material are formed. H+(added) is moles acid added in excess of the moles of hydroxide added. In calculating H+(added) and OH values, the term acid (H+) includes both hydronium ion, whether free or coordinated, and aluminum. Thus aluminum sulfate, for example, would be considered a mixture of aluminum oxide, sulfuric acid, and water. An amine hydrochloride would be a mixture of amine and HCl. In preparing the highly siliceous form of ZSM-48 no alumina is added. Thus, the only aluminum present occurs as an impurity in the reactants.

Preferably, crystallization is carried out under pressure in an autoclave or static bomb reactor, at 80° C. to 250° C. Thereafter, the crystals are separated from the liquid and recovered. The composition can be prepared utilizing materials which supply the appropriate oxide. Such compositions include sodium silicate, silica hydrosol, silica gel, silicic acid, RN, sodium hydroxide, sodium chloride, aluminum sulfate, sodium aluminate, aluminum oxide, or aluminum itself. RN is a $C_1$–$C_{20}$ organic compound containing at least one amine functional group of $pk_a \leq 7$, as defined above, and includes such compounds as $C_3$–$C_{18}$ primary, secondary, and tertiary amines, cyclic amine (such as piperdine, pyrrolidine and piperazine), and polyamines such as $NH_2$-$C_nH_{2n}$-$NH_2$ wherein n is 4–12.

The original cations can be subsequently replaced, at least in part, by calcination and/or ion exchange with another cation. Thus, the original cations are exchanged into a hydrogen or hydrogen ion precursor form or a form in which the original cation has been replaced by a metal of Groups II through VIII of the Periodic Table. Thus, for example, it is contemplated to exchange the original cations with ammonium ions or with hydronium ions. Catalytically active forms of these would include, in particular, hydrogen, rare earth metals, aluminum, manganese and other metals of Groups II and VIII of the Periodic Table.

It is to be understood that by incorporating by reference the foregoing patents to describe examples of specific members of the novel class with greater particularity, it is intended that identification of the therein disclosed crystalline zeolites be resolved on the basis of their respective X-ray diffraction patterns. As discussed above, the present invention contemplates utilization of such catalysts wherein the mole ratio of silica to alumina is essentially unbounded. The incorporation of the identified patents should therefore not be construed as limiting the disclosed crystalline zeolites to those having the specific silica-alumina mole ratios discussed therein, it now being known that such zeolites may be substantially aluminum-free and yet, having the same crystal structure as the disclosed materials, may be useful or even preferred in some applications. It is the crystal structure, as identified by the X-ray diffraction "fingerprint", which establishes the identity of the specific crystalline zeolite material.

The specific zeolites described, when prepared in the presence of organic cations, are substantially catalytically inactive, possibly because the intra-crystalline free space is occupied by organic cations from the forming solution. They may be activated by heating in an inert atmosphere at 540° C. for one hour, for example, followed by base exchange with ammonium salts followed by calcination at 540° C. in air. The presence of organic cations in the forming solution may not be absolutely essential to the formation of this type zeolite; however, the presence of these cations does appear to favor the formation of this special class of zeolite. More generally, it is desirable to activate this type catalyst by base exchange with ammonium salts followed by calcination in air at about 540° C. for from about 15 minutes to about 24 hours.

Natural zeolites may sometimes be converted to zeolite structures of the class herein identified by various activation procedures and other treatments such as base exchange, steaming, alumina extraction and calcination, alone or in combinations. Natural minerals which may be so treated include ferrierite, brewsterite, stilbite, dachiardite, epistilbite, heulandite, and clinoptilolite.

The preferred crystalline zeolites for utilization herein include ZSM-5, ZSM-11, ZSM-12, ZSM-23, ZSM-35, ZSM-38 and ZSM-48, with ZSM-5 being particularly preferred.

In a preferred aspect of this invention, the zeolites hereof are selected as those providing among other things a crystal framework density, in the dry hydrogen form, of not less than about 1.6 grams per cubic centimeter. It has been found that zeolites which satisfy all three of the discussed criteria are most desired for several reasons. When hydrocarbon products or by-products are catalytically formed, for example, such zeolites tend to maximize the production of gasoline boiling range hydrocarbon products. Therefore, the preferred zeolites useful with respect to this invention are those having a Constraint Index as defined above of about 1 to about 12, a silica to alumina mole ratio of at least about 12 and a dried crystal density of not less than about 1.6 grams per cubic centimeter. The dry density for known structures may be calculated from the number of silicon plus aluminum atoms per 1000 cubic Angstroms, as given, e.g., on Page 19 of the article ZEOLITE STRUCTURE by W. M. Meier. This paper, the entire contents of which are incorporated herein by reference, is included in PROCEEDINGS OF THE CONFERENCE ON MOLECULAR SIEVES, (London, April 1967) published by the Society of Chemical Industry, London, 1968.

When the crystal structure is unknown, the crystal framework density may be determined by classical pycnometer techniques. For example, it may be determined by immersing the dry hydrogen form of the zeolite in an organic solvent which is not sorbed by the crystal. Or, the crystal density may be determined by mercury porosimetry, since mercury will fill the interstices between crystals but will not penetrate the intracrystalline free space.

It is possible that the unusual sustained activity and stability of this special class of zeolites is associated with its high crystal anionic framework density of not less than about 1.6 grams per cubic centimeter. This high density must necessarily be associated with a relatively small amount of free space within the crystal, which might be expected to result in more stable structures. This free space, however, is important as the locus of catalytic activity.

Crystal framework densities of some typical zeolites, including some which are not within the purview of this invention, are:

|  | Void Volume | Framework Density |
|---|---|---|
| Ferrierite | 0.28 cc/cc | 1.76 g/cc |

| | Void Volume | Framework Density |
|---|---|---|
| Mordenite | .28 | 1.7 |
| ZSM-5, -11 | .29 | 1.79 |
| ZSM-12 | — | 1.8 |
| ZSM-23 | — | 2.0 |
| Dachiardite | .32 | 1.72 |
| L | .32 | 1.61 |
| Clinoptilolite | .34 | 1.71 |
| Laumontite | .34 | 1.77 |
| ZSM-4 (Omega) | .38 | 1.65 |
| Heulandite | .39 | 1.69 |
| P | .41 | 1.57 |
| Offretite | .40 | 1.55 |
| Levynite | .40 | 1.54 |
| Erionite | .35 | 1.51 |
| Gmelinite | .44 | 1.46 |
| Chabazite | .47 | 1.45 |
| A | .5 | 1.3 |
| Y | .48 | 1.27 |

When synthesized in the alkali metal form, the zeolite is conveniently converted to the hydrogen form, generally by intermediate formation of the ammonium form as a result of ammonium ion exchange and calcination of the ammonium form to yield the hydrogen form. In addition to the hydrogen form, other forms of the zeolite wherein the original alkali metal has been reduced to less than about 1.5 percent by weight may be used. Thus, the original alkali metal of the zeolite may be replaced by ion exchange with other suitable metal cations of Groups I through VII of the Periodic Table, including, by way of example, nickel, copper, zinc, palladium, calcium or rare earth metals.

In practicing a particularly desired chemical conversion process, it may be useful to incorporate the above-described crystalline zeolite with a matrix comprising another material resistant to the temperature and other conditions employed in the process. Such matrix material is useful as a binder and imparts greater resistance to the catalyst for the severe temperature, pressure and reactant feed stream velocity conditions encountered in many cracking processes.

Useful matrix materials include both synthetic and naturally occurring substances, as well as inorganic materials such as clay, silica and/or metal oxides. The latter may be either naturally occurring or in the form of gelatinous precipitates or gels including mixtures of silica and metal oxides. Naturally occurring clays which can be composited with the zeolite include those of the montmorillonite and kaolin families, which families include the sub-bentonites and the kaolins commonly known as Dixie, McNamee-Georgia and Florida clays or others in which the main mineral constituent is halloysite, kaolinite, dickite, nacrite or anauxite. Such clays can be used in the raw state as originally mined or initially subjected to calcination, acid treatment or chemical modification.

In addition to the foregoing materials, the zeolites employed herein may be composited with a porous matrix material, such as alumina, silica-alumina, silica-magnesia, silica-zirconia, silica-thoria, silica-beryllia, and silica-titania, as well as ternary compositions, such as silica-alumina-thoria, silica-alumina-zirconia, silica-alumina-magnesia and silica-magnesia-zirconia. The matrix may be in the form of a cogel. The relative proportions of zeolite component and inorganic oxide gel matrix, on an anhydrous basis, may vary widely with the zeolite content ranging from between about 1 to about 99 percent by weight and more usually in the range of about 5 to about 80 percent by weight of the dry composite.

DESCRIPTION OF SPECIFIC EXAMPLES

EXAMPLE 1

Figure 2:
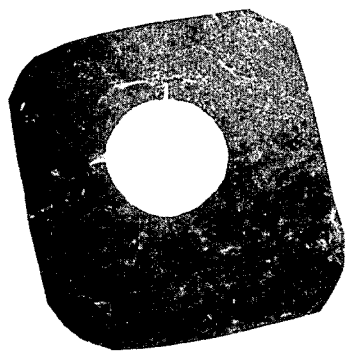
FIG. 2 is a photolithographic reproduction of a cross section of another preferred form of catalyst particle in accordance with the present invention.
Figure 3:
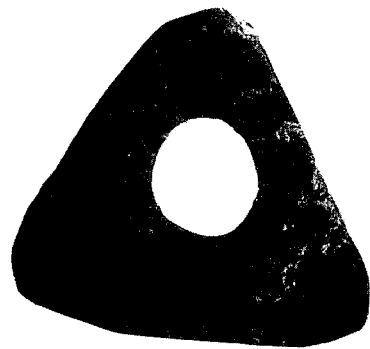
FIG. 3 is a photolithographic reproduction of a cross section of still another preferred form of catalyst particle in accordance with the present invention.
Figure 7:
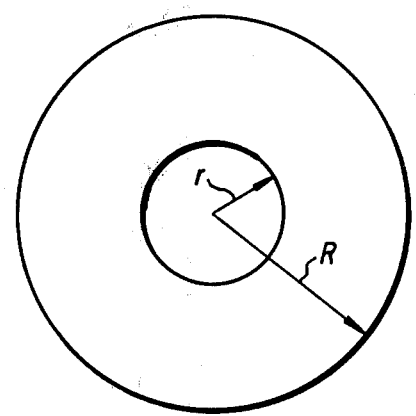
FIG. 7 is a graphic representation of a cross-section of a prior art tubular cylindrical catalyst particle configuration.

The different catalyst shapes as illustrated in FIGS. 1 through 6 inclusive of the accompanying drawings and a cylindrical tubular shape as illustrated in FIG. 7 were extruded from the following catalyst composition. The catalyst composition comprised approximately 65% by weight of NaZSM-5 and about 35% by weight of alumina. More specifically aggregates of NaZSM-5 zeolite, 580.3 g, (at 87.6% solids) were mulled in a small batch mixer for about 90 minutes to a fine, uniform powder. To the zeolite, 368.7 g (74.4% solids) of alpha monohydrate alumina and 16 g of a cellulose type extrusion aid were added and the composition was mixed and mulled for 20 minutes. Deionized water, 633.8 g, was then slowly added to the mix, after which mulling was continued for 60 minutes. By calculation the extrusion mix contained 49% solids. The mix was then extruded at ambient temperature by a hydraulic press. A die plate with the desired orifice configuration was mounted on the outlet end of the extruder. It will be obvious that the die plate orifice will determine the final configuration of the shaped extrudate as illustrated in FIGS. 1, 2, and 3. The catalyst mix was compacted and extruded out of the respective die orifice. Following extrusion, the catalyst was dried over night at 220° F.–250° F. and stored.

The size of the specific catalysts fabricated as well as their crushing strengths, particle densities, and other physical characteristics are described in the following Table 1.

TABLE 1

| PHYSICAL PROPERTIES OF TUBULAR SHAPED EXTRUDATES | | | | |
|---|---|---|---|---|
| Reference | Cylindrical Tube | FIG. 1 Tube | FIG. 2 Tube | FIG. 3 Tube |
| Extrudate Wall Thickness, in. | 0.0390 | 0.0117–0.0390 | 0.0283–0.040 | 0.020–0.040 |
| Nominal Size (O.D.)in. | ⅛ | ⅛ | ⅛ | ⅛ |
| Cross-sectional Area, in.$^2$ | 0.009943 | 0.006816 | 0.007732 | 0.006235 |
| Average Length, in. | Not measured | 0.2519 | 0.260 | 0.246 |
| Vp/Sp, in. | Not determined | 0.01240 | 0.01439 | 0.0116 |
| *Crush Strength, lbs/in. | | | | |
| Average | 38.8 | 119.9 | 74.8 | 41.3 |
| Range | 22–58 | 80–157 | 39–129 | 22–82 |
| Crush Strength/Extrudate Volume (Tons/cu. in.) | 1.95 | 8.80 | 4.85 | 3.29 |
| Particle Density (mercury displacement) g/cc | 0.855 | 0.848 | 0.856 | 0.860 |
| **Pressure Drop, in. H$_2$O/ft (N$_2$ mass flow rate) | | | | |

TABLE 1-continued

| | PHYSICAL PROPERTIES OF TUBULAR SHAPED EXTRUDATES | | | |
|---|---|---|---|---|
| Reference | Cylindrical Tube | FIG. 1 Tube | FIG. 2 Tube | FIG. 3 Tube |
| 1000 lb/ft$^2$ hr | — | 9.1 | 11.2 | 12.7 |
| 2000 lb/ft$^2$ hr | — | 28.0 | 33.7 | 35.7 |

*In the Crushing Strength Test, a calcined extruded particle was placed on its side between two parallel, horizontal flat plates, one stationary and one movable. A gradually increasing force was applied to the movable plate perpendicular to the surface of the plate, until the particle broke. The crushing strength is the force in pounds applied at the instant particle breakage occurs. The crushing strength reported is the average value determined on 25 particles. The crushing test strength is related to the ability of the catalyst to withstand pressure drops and to support the catalyst bed in the reactor.
**For test description cf. Sabri Ergun, Anal. Chem. 23,151 (1951)

EXAMPLE 2

The different catalyst shapes as illustrated in FIGS. 1 through 6 inclusive of the accompanying drawings were extruded from the following catalyst composition. The catalyst composition comprised approximately 65% by weight of NaLSM5 and about 35% by weight of alumina. More specifically aggregates of NaZSM-5 zeolite, 2450.5 g, (at 88.3% solids) were mulled in a small batch mixer for about 30 minutes to a fine, uniform powder. To the zeolite, 1642.7 g (71.0% solids) of alpha monohydrate alumina and 30 g of a cellulose type extrusion aid were added and the composition was mixed and mulled for 20 minutes. Deionized water, 1876.8 g, was then slowly added to the mix, after which mulling was continued for 30 minutes. By calculation the extrusion mix contained 55.5% solids. The mix was then extruded at ambient temperature by an auger extruder. A die plate with the desired orifice configuration was mounted on the outlet end of the extruder. It will be obvious that the die plate orifice will determine the final configuration of the shaped extrudate. The catalyst mix was extruded out of the respective die orifice. Following extrusion, the catalyst was dried overnight at 220° F.-250° F. and stored.

The size of the specific catalysts fabricated as well as their crushing strengths, and particle densities, are described in the following Table 2.

TABLE 2

| PHYSICAL PROPERTIES OF TUBULAR SHAPED EXTRUDATES | | | |
|---|---|---|---|
| Reference | FIG. 1 Tube | FIG. 2 Tube | FIG. 3 Tube |
| Extrudate Wall Thickness, in. | 0.0117–0.0390 | 0.0283–0.040 | 0.020–0.040 |
| Nominal Size (O.D.)in. | ⅛ | ⅛ | ⅛ |
| Cross-sectional Area, in.$^2$ | 0.006816 | 0.007732 | 0.006235 |
| *Crush Strength, lbs/in. | | | |
| Average | 95.1 | 62.3 | 31.8 |
| Range | 55–160 | 41–118 | 19–62 |
| Crush Strength/Extrudate Volume (Tons/cu. in.) | 6.98 | 4.03 | 2.55 |
| Particle Density (mercury displacement) g/cc | 1.017 | 1.034 | 1.030 |

EXAMPLE 3

A catalyst with the shape as illustrated in FIG. 1 of the accompanying drawings and a catalyst with a cylindrical tubular shape as illustrated in FIG. 7 were extruded from the following catalyst composition. The catalyst composition comprised approximately 65% by weight of NaZSM-5 and about 35% by weight of alumina. More specifically aggregates of NaZSM-5 zeolite, 556.6 g, (at 87.8% solids) were mulled in a small batch mixer for about 90 minutes to a fine, uniform powder. To the zeolite, 353.7 g (74.4% solids) of alpha monohydrate alumina and 16 g of a cellulose type extrusion aid were added and the composition was mixed and mulled for 20 minutes. Deionized water, 673.7 g, was then slowly added to the mix, after which mulling was continued for 60 minutes. By calculation the extrusion mix contained 47% solids. The mix was then extruded at ambient temperature by a hydraulic press. A die plate with the desired orifice configuration was mounted on the outlet end of the extruder. Following extrusion, the catalyst was dried over night at 220° F.-250° F. and stored.

The size of the specific catalysts fabricated as well as their crushing strengths, densities, and other physical characteristics are described in the following Table 3.

TABLE 3

| PHYSICAL PROPERITIES OF TUBULAR SHAPED EXTRUDATES | | |
|---|---|---|
| Reference | Cylindrical Tube | FIG. 1 Tube |
| Extrudate Wall Thickness, in. | 0.0390 | 0.0117–0.0390 |
| Nominal Size (O.D.)in. | ⅛ | ⅛ |
| Cross-sectional Area, in.$^2$ | 0.009943 | 0.006816 |
| Average Length, in. | 0.2776 | 0.2215 |
| Vp/Sp, in. | 0.0171 | 0.0122 |
| *Crush Strength, lbs/in. | | |
| Average | 18.0 | 88.1 |
| Range | 10–25 | 65–120 |
| Crush Strength/Extrudate Volume (Tons/cu. in.) | 0.91 | 6.46 |
| Particle Density (mercury displacement) g/cc | 0.841 | 0.861 |
| **Pressure Drop, in. H$_2$O/ft (N$_2$ mass flow rate) | | |
| 1000 lb/ft$^2$ hr | 8.2 | 10.5 |
| 2000 lb/ft$^2$ hr | 25.1 | 31.9 |

EXAMPLE 4

Conventional cylindrical shaped catalysts of three different sizes, i.e. 1/25 inch, 1/16 inch and ⅛ inch diameter, were extruded from the following catalyst composition. The catalyst composition comprised approximately 65% by weight of NaZSM-5 and about 35% by weight of alumina. More specifically, aggregates of NaZSM-5 zeolite (87.8% solids), 568.5 g, were mulled in a small batch mixer for about 90 minutes to a fine, uniform power. To the zeolite, 361.2 g of alpha monohydrate alumina at 74.4% solids and 16 g of a cellulose type extrusion aid were added and the composition was mixed and mulled for 20 minutes. Deionized water, 654.3 g, was then slowly added to the mix, after which mulling was contained for 60 minutes. By calculation, the extrusion mix contained 48% solids. The mix was then extruded at ambient temperature by a hydraulic press. The formed catalyst was dried over night at 220°–250° F. and stored.

The size of the specific catalysts fabricated as well as their crushing strengths, particle densities and other physical characteristics are described in Table 4. The advantage of reduced pressure drops of the novel shaped catalysts as illustrated in previous examples becomes apparent when compared to 1/25 inch or 1/16 inch cylindrical shaped catalysts described in this example.

EXAMPLE 6

The 1/25 inch and ⅛ inch cylindrical catalysts were extruded from the following catalyst composition. The catalyst composition comprised approximately 65% by weight of NaZSM-5 and about 35% by weight of alumina. More specifically aggregates of NaZSM-5 zeolite, 2229.5 g, (at 88.3% solids) were mulled in a small batch mixer for about 30 minutes to a fine, uniform powder. To the zeolite, 1447.0 g (73.3% solids) of alpha monohydrate alumina was added and the composition was mixed and mulled for 20 minutes. Deionized water, 2323.0 g, was then slowly added to the mix, after which mulling was continued for 30 minutes. By calculation the extrusion mix contained 50.5% solids. The mix was then extruded at ambient temperature by an auger extruder. A die plate with the desired orifice configuration was mounted on the outlet end of the extruder. It will be obvious that the die plate orifice will determine the final configuration of the shaped extrudate. The

TABLE 4

| PHYSICAL PROPERTIES OF CYLINDRICAL SHAPED EXTRUDATES | | | |
|---|---|---|---|
| Reference | 1/25" Cylinder | 1/16" Cylinder | ⅛" Cylinder |
| Nominal Size (O.D.)in. | 1/25 | 16 | ⅛ |
| Cross-sectional Area, in.$^2$ | 0.00126 | 0.00267 | 0.01227 |
| Average Length, in. | 0.1314 | 0.1829 | 0.2668 |
| Vp/Sp, in. | 0.00845 | 0.01257 | 0.02477 |
| *Crush Strength, lbs/in. | | | |
| Average | 29.3 | 40.1 | 47.9 |
| Range | 16–45 | 25–56 | 27–72 |
| Crush Strength/Extrudate Volume (Tons/cu. in.) | 11.6 | 7.5 | 2.0 |
| Particle Density (mercury displacement) g/cc | 0.861 | 0.860 | 0.852 |
| **Pressure Drop, in. H$_2$O/ft ($N_2$ mass flow rate) | | | |
| 1000 lb/ft$^2$ hr | 39.8 | 24.7 | 10.5 |
| 2000 lb/ft$^2$ hr | 108.9 | 71.5 | 32.1 |

EXAMPLE 5

The different catalyst shapes as illustrated in FIGS. 2, 3 and 7 of the accompanying drawings were extruded from the following cataflyst composition. The catalyst composition comprised approximately 65% by weight of NaZSM-5 and about 35% by weight of alumina. More specifically aggregates of NaZSM-5 zeolite, 2207.6 g, (at 88.3% solids) were mulled in a small batch mixer for about 30 minutes to a fine, uniform powder. To the zeolite, 1479.9 g (73.3% solids) of alpha monohydrate alumina was added and the composition was mixed and mulled for 20 minutes. Deionized water, 2312.5 g, was then slowly added to the mix, after which mulling was continued for 30 minutes. By calculation the extrusion mix contained 50.6% solids. The mix was then extruded at ambient temperature by an auger extruder. A die plate with the desired orifice configuration was mounted on the outlet end of the extruder. It will be obvious that the die plate orifice will determine the final configuration of the shaped extrudate. The catalyst mix was extruded out of the respective die orifice. Following extrusion, the catalyst was dried overnight at 250° F. and stored.

The size of the specific catalysts fabricated as well as their crushing strengths, densities, and other physical characteristics are described in the following Table 5.

catalyst mix was compacted and extruded out of the respective die orifice. Following extrusion, the catalyst was dried over night at 250° F. and stored.

The size of the specific catalysts fabricated as well as their crushing strengths, densities, and other physical characteristics are described in Table 5.

EXAMPLE 7

The 1/16 inch cylindrical catalyst and catalyst shaped as illustrated in FIG. 1 were extruded from the following catalyst composition. The catalyst composition comprised approximately 65% by weight of NaZSM-5 and about 35% by weight of alumina. More specifically aggregates of NaZSM-5 zeolite, 2207.6 g, (88.3% solids) were mulled in a small batch mixer for about 30 minutes to a fine, uniform powder. To the zeolite, 1432.7 g (73.3% solids) of alpha monohydrate alumina and 15.0 g of a cellulose type extrusion aid were added and the composition was mixed and mulled for 20 minutes. Deionized water, 2344.7 g, was then slowly added to the mix, after which mulling was continued for 30 minutes. By calculation the extrusion mix contained 50% solids. The mix was then extrudated at ambient temperature by an auger extruder. A die plate with the desired orifice configuration was mounted on the outlet end of the extruder. It will be obvious that the die plate orefice will determine the final configuration of the shaped extrudate. The catalyst mix was compacted and extruded out of the respective die orifice. Following extrusion, the catalyst was dried over night at 250° F. and stored.

The size of the specific catalysts fabricated as well as their crushing strengths, densities, and other physical characteristics are described in Table 5.

tion, which employ Friedel-Crafts catalyst, most commonly, aluminum chloride in a mixed liquid-gas-phase reaction system). A more detailed description of the alkylation process may be found in U.S. Pat. Nos. 3,751,506 and 3,751,504, the disclosures of which are

TABLE 5

(Examples 5, 6, & 7)
PHYSICAL PROPERTIES OF TUBULAR SHAPED EXTRUDATES

| Reference | Cylindrical FIG. 7 Tube | FIG. 1 Tube | FIG. 2 Tube | FIG. 3 Tube | Solid 1/25" Cylinder | Solid 1/16" Cylinder | Solid ⅛" Cylinder |
|---|---|---|---|---|---|---|---|
| Nominal Size (O.D.)in. | ⅛ | ⅛ | ⅛ | ⅛ | 1/25 | 1/16 | ⅛ |
| Cross-sectional Area, in.² | 0.009943 | 0.006816 | 0.007732 | 0.006235 | 0.001257 | 0.003068 | 0.012272 |
| Average Length, in. | 0.204 | 0.249 | 0.206 | 0.222 | 0.183 | 0.204 | 0.238 |
| Vp/Sp, in. | 0.0213 | 0.0117 | 0.0134 | 0.0114 | 0.0090 | 0.0141 | 0.0243 |
| *Crush Strength, lbs/in. | | | | | | | |
| Average | 27.0 | 101.9 | 51.1 | 25.2 | 47.1 | 55.0 | 64.4 |
| Range | 17–36 | 65–128 | 32–78 | 17–39 | 28–66 | 34–85 | 40–105 |
| Crush Strength/Extrudate Volume (Tons/cu. in.) | 1.4 | 7.5 | 3.3 | 2.0 | 18.7 | 9.0 | 2.6 |
| Particle Density (mercury displacement) g/cc | 0.875 | 0.888 | 0.889 | 0.911 | 0.905 | 0.901 | 0.873 |
| **Pressure Drop, in. H₂O/ft (N₂ mass flow rate) | | | | | | | |
| 1000 lb/ft² hr | 11.6 | 10.8 | 12.9 | 17.6 | 24.5 | 20.7 | 12.3 |
| 2000 lb/ft² hr | 33.3 | 32.2 | 37.0 | 49.5 | 65.7 | 57.3 | 36.2 |

It is apparent from the data presented in the foregoing Tables that the novel shaped tubular extrudates in accordance with the present invention have vastly superior resistance to crushing forces when compared to the prior art cylindrical tube shaped extrudates.

As hereinbefore noted, the novel catalyst structures in accordance with the present invention may be employed in a variety of catalytically activated processes, as hereinabove described for example, hydroprocessing, dealkylation and alkylation including the alkylation of benzene, for example, the alkylation of benzene with ethylene to form ethylbenzene; processes such as the conversion of methanol to petrochemicals and gasoline; and isomerization processes such as, for example, xylene isomerization including vapor phase isomerization, high temperature isomerization, low pressure isomerization, de-ethylation isomerization and isomerization employing severe processing conditions. Included among the various processes which may be enhanced by employment of the catalyst structure of the present invention are processes such as dewaxing, isomerization, and the conversion of lower alkanols to petrochemicals and gasoline. Such processes are described in U.S. Pat. Nos. 4,292,166; 4,247,388; 4,094,921; 4,236,996; and 4,138,440, the disclosures of which are incorporated herein by reference. In the following specific examples the catalyst structures of the present invention were employed, to illustrate the effectiveness of the present catalyst shapes in a benzene alkylation process and, more specifically an ethylbenzene process. The ethylbenzene process described hereinafter employs a solid, non-Friedel-Crafts catalyst to alkylate benzene with ethylene in contrast to other commercially known processes for the manufacture of ethylbenzene (the feedstock, for example, for styrene production, which employ Friedel-Crafts catalyst, most commonly, aluminum chloride in a mixed liquid-gas-phase reaction system). A more detailed description of the alkylation process may be found in U.S. Pat. Nos. 3,751,506 and 3,751,504, the disclosures of which are incorporated herein by reference.

BENZENE ALKYLATION USING PRIOR ART CATALYST SHAPES AND CATALYST SHAPES OF THE PRESENT INVENTION

EXAMPLE 8

A ZSM-5 containing catalyst of FIG. 1 configuration was charged to a flow tubular reactor and the alkylation reaction was conducted at a total pressure of 300 psig, WHSV of 4 grams of ethylene per gram of catalyst per hour and at a benzene/ethylene mole ratio of 10, and at a constant inlet temperature of 770° F. The conversion of ethylene at greater than 96.5% was maintained for 3 days. The diethylbenzene (DEB) to ethylbenzene (EB) ratio in the product increased from 0.071 to 0.073 over the course of the run.

Catalysts of other configurations were tested under similar reaction conditions. The ethylene conversion, the length of time at which it was maintained, and the diethylbenzene to ethylbenzene ratio in the product for all catalyst configurations are shown in the following Table 6. In the same table, typical physical properties of all catalyst configurations are also shown.

From the table, it is apparent that the catalyst configurations of the present invention have higher ethylene conversions, longer cycle time, lower diethylbenzene to ethylbenzene ratios, higher crushing strengths over the prior art, cylinderical tubular form and ⅛ inch cylinder. Although the catalytic activity on catalyst configurations of the present invention is approximately the same or slightly lower than that on 1/16 inch or 1/25 inch cylinder, the advantages of reduced pressure drop and high crushing strengths are realized.

TABLE 6

| CATALYST CONFIGURATION | FIG. 1 Tube | FIG. 3 Tube | Cylindrical Tube | ⅛"solid Cylinder | 1/16"solid Cylinder | 1/25"solid Cylinder |
|---|---|---|---|---|---|---|
| Catalytic Properties | | | | | | |
| Ethylene Conversion % | 96.5 (min) | 96 (min) | 95.1 (min) | 91.4–88.6 | 97 (min) | 97.5 (min) |
| Length of time the conversion was maintained, days | 3 | 4 | 1 | 2 | 4 | 6 |
| DEB/EB Ratio | 0.071–0.073 | 0.093–0.098 | 0.086 | 0.09 | 0.080–0.085 | 0.060–0.069 |

TABLE 6-continued

| CATALYST CONFIGURATION | FIG. 1 Tube | FIG. 3 Tube | Cylindrical Tube | ⅛"solid Cylinder | 1/16"solid Cylinder | 1/25"solid Cylinder |
|---|---|---|---|---|---|---|
| Typical Physical Properties of Catalyst Particles | | | | | | |
| Vp/Sp, in. | 0.0124 | 0.0116 | 0.0171 | 0.02487 | 0.0126 | 0.0085 |
| Pressure Drop, in. $H_2O$/ft ($N_2$ mass flow rate) 2000 lb/ft² hr | 28 | 36 | 25 | 32 | 70 | 110 |
| Crushing Strength, lbs/in. | 120 | 34 | 14 | 60 | 50 | 30 |

Reaction Conditions: 770° F. inlet temperature, 4 WHSV ethylene, Benzene/ethylene = 10/1 (mole), 300 psig total pressure.

EXAMPLE 9

A NaZSM-5 containing catalyst of FIG. 1 configuration was calcined in nitrogen, ammonia exchanged, and further calcined in air to yield the acidic HZSM-5 form. The catalyst was charged to a flow tubular reactor and the reaction of methanol (83% wt.) and $H_2O$ (17% wt.) charge was conducted at a total pressure of 300 psig, WHSV of 1.6 methanol, at a helium to methanol ractio of 9 to 1, and at a hot spot temperature of 776° F. Similarly, a HZSM-5 containing catalyst of ⅛ inch solid cylindrical configuration was tested. The product distribution of the two catalyst configurations is compared in Table 7. It can be seen that the novel shape of the catalyst of the present invention gives methanol conversion products which have higher yields of gasoline range constituents, but lower yields of light gases than the prior art shape.

TABLE 7

REACTION OF METHANOL OVER HZSM-5 CATALYST

| Particle Configuration | FIG. 1 Tube | ⅛" Solid Cylinder | FIG. 1 Tube | ⅛" Solid Cylinder |
|---|---|---|---|---|
| Temperature, °F. | 776 | 776 | 775 | 775 |
| Time on Stream, hrs | 20.0 | 20.5 | 68.0 | 92.8 |
| Product Distribution Wt.%, HC | | | | |
| C1 | 0.02 | 0.28 | 0.06 | 0.34 |
| C2 | 0.17 | 0.55 | 0.27 | 0.34 |
| C2= | 0.11 | 0.67 | 0.50 | 2.36 |
| C3 | 3.50 | 11.90 | 4.56 | 5.98 |
| C3= | 0.15 | 1.16 | 0.60 | 3.43 |
| C to C3 subtotal | (3.95) | (14.56) | (5.99) | (12.45) |
| IC4 | 6.02 | 14.91 | 9.79 | 12.44 |
| NC4 | 1.82 | 3.41 | 2.12 | 2.19 |
| C4= | 0.26 | 0.85 | 0.98 | 3.09 |
| Total C4 | (8.10) | (19.17) | (12.89) | (17.72) |
| IC5 | 9.62 | 7.92 | 10.82 | 9.72 |
| NC5 | 1.06 | 0.79 | 1.18 | 1.00 |
| C5= | 0.34 | 0.22 | 0.88 | 1.08 |
| C6 P+N | 9.85 | 6.57 | 12.84 | 11.53 |
| C6= | 0.31 | 0.21 | 0.51 | 0.64 |
| Benzene | 0.69 | 0.35 | 0.46 | 0.31 |
| C7 P+O+N | 2.95 | 1.84 | 5.85 | 4.98 |
| Toluene | 5.86 | 3.27 | 3.54 | 2.02 |
| C8 P+O+N | 0.90 | 0.64 | 2.31 | 2.25 |
| C8 A | 16.68 | 11.74 | 11.53 | 9.04 |
| C9 P+O+N+A | 16.89 | 13.54 | 14.46 | 13.05 |
| C10 P+O+N+A | 10.92 | 7.19 | 6.04 | 3.36 |
| Durene | 9.65 | 10.43 | 9.10 | 9.64 |
| C11-C12 P+O+N+A | 0.63 | 0.32 | 0.98 | 0.75 |
| Naphthalenes | 1.37 | 1.15 | 0.47 | 0.36 |
| C13 +'S | 0.25 | 0.12 | 0.14 | 0.09 |
| C5+ subtotal | (87.97) | (66.27) | (81.11) | (69.82) |
| Wt.% CH2 Conv. | 100.00 | 100.00 | 100.00 | 100.00 |
| HC recovery % theo. | 91.47 | 106.58 | 96.52 | 107.96 |

Charge: 83 Wt. % $CH_3OH$, 17 Wt. % $H_2O$
300 psig, 1.60 WHSV $CH_3OH$, He/$CH_3OH$ = 9
P—paraffins, O—Olefins, N—Naphthenes, A—aromatics

What is claimed is:

1. A catalyst particle having a non-cylindrical centrally located aperture surrounded by a solid wall portion, a volume to surface ratio of less than about 0.02 inch and an external periphery characterized by having at least 3 points of contact when circumscribed by a cylindrical shape.

2. A catalyst particle in accordance with claim 1 having at least 3 and no more than 10 points of contact when circumscribed by said cylindrical shape.

3. A catalyst particle in accordance with claim 1 having at least 3 and no more than 4 points of contact when circumscribed by said cylindrical shape.

4. A particle in accordance with claim 1 wherein said solid wall portion has a maximum thickness of R-r wherein R is the radius of a cylinder which circumscribes the particle and r is the radius of said aperture, said particle being further characterized in that the value of R/r may vary about 1.1 up to about 10.

5. A particle in accordance with claim 1 wherein said external periphery wall portion is in the form of an essentially rectangular configuration.

6. A particle in accordance with claim 1 wherein said particle external periphery is characterized by having at least one protuberance and at least one concave surface.

7. A particle in accordance with claim 1 wherein said external periphery is characterized by having an essentially triangle-like configuration.

8. A catalyst particle in accordance with claim 1 wherein said particle comprises a member selected from the group consisting of alumina, silica, aluminosilicates, clay and mixtures thereof.

9. A catalyst particle in accordance with claim 1 wherein said particle comprises a zeolite.

10. A catalyst particle in accordance with claim 9 wherein said zeolite comprises ZSM-5.

11. A catalyst particle in accordance with claim 1 wherein said particle comprises a mixture of alumina and a zeolite.

12. A catalyst particle in accordance with claim 1 wherein said particle comprises a mixture of silica and zeolite.

13. A catalyst particle in accordance with claim 1 wherein said particle comprises a mixture of silica-alumina and zeolite.

14. A catalyst particle in accordance with claim 1 wherein said particle comprises a mixture of clay and zeolite.

15. A process for the conversion of an organic charge which comprises contacting the same under conversion conditions with a catalyst comprising a crystalline aluminosilicate characterized by having a formed non-cylindrical particle configuration comprising a centrally located aperture surrounded by a solid wall portion, a volume to surface ratio of less than about 0.02 inch and an external periphery characterized by having at least 3 points of contact when circumscribed by a cylindrical shape.

16. The process of claim 15 wherein said crystalline aluminosilicate is a zeolite, said zeolite being characterized by a SiO$_2$:Al$_2$O$_3$ ratio of greater than 5.

17. The process of claim 15 wherein said crystalline aluminosilicate zeolite is combined with a binder in an amount less than about 90 weight percent.

18. The process of claim 17 wherein said binder is alumina.

19. The process of claim 17 wherein said binder is silica.

20. The process of claim 17 wherein said binder is a mixture of silica and alumina.

21. The process of claim 17 wherein said binder is clay.

22. The process of claim 15 wherein said charge comprises an oxygenate.

23. The process of claim 22 wherein said oxygenate is selected from the group consisting of methanol, ethanol, ether derivatives of lower alcohols and mixtures of alcohols and ethers.

24. The process of claim 23 wherein said methanol is converted to gasoline boiling range constituents.

25. The process of claim 23 wherein methanol is converted to lower olefins.

26. The process of claim 23 wherein methanol is converted to materials containing two or more carbon atoms.

27. The process of claim 15 wherein said charge comprises a hydrocarbon.

28. The process of claim 27 wherein said conversion comprises alkylation of an aromatic hydrocarbon.

29. The process of claim 27 wherein said conversion comprises alkylation of benzene.

30. The process of claim 28 wherein said alkylating agent is ethylene.

31. The process of claim 28 wherein said alkylating agent is propylene.

32. The process of claim 27 wherein said conversion comprises the ethylation of mono alkyl benzene.

33. The process of claim 32 wherein said alkyl substituent contains 1 to 2 carbon atoms.

34. The process of claim 27 wherein said hydrocarbon conversion comprises xylene isomerization.

35. The process of claim 27 wherein said hydrocarbon conversion comprises oligomerization of olefins.

36. The process of claim 27 wherein said conversion comprises cracking of a hydrocarbon charge.

37. The process of claim 27 wherein said hydrocarbon conversion comprises disproportionation of toluene to produce benzene and xylenes in which the proportion of para-xylene isomer is in excess of its normal equilibrium concentration.

38. The process of claim 27 wherein said charge comprises a hydrocarbon oil feedstock boiling above 650° F. (343° C.) and selected from the group consisting of vacuum gas oils, deasphalted oils, and mixtures thereof, said charge being converted to low-pour point, high V.I., lube basestock.

39. The process of claim 27 wherein said conversion involves hydrodewaxing of a petroleum or synthetic hydrocarbon charge.

* * * * *

UNITED STATES PATENT AND TRADEMARK OFFICE
CERTIFICATE OF CORRECTION

PATENT NO. : 4,441,990
DATED : April 10, 1984
INVENTOR(S) : Yun-Yang Huang

It is certified that error appears in the above—identified patent and that said Letters Patent is hereby corrected as shown below:

Column 19, line 66, change in Claim 1, line 1, "A catalyst particle having a non-cylindrical" to ---A non-cylindrical catalyst particle having a---

Signed and Sealed this

Twenty-third Day of October 1984

[SEAL]

Attest:

GERALD J. MOSSINGHOFF

Attesting Officer

Commissioner of Patents and Trademarks